United States Patent [19]

Wilhelm

[11] Patent Number: 4,967,573
[45] Date of Patent: Nov. 6, 1990

[54] THERMAL PACK

[76] Inventor: Raymond P. Wilhelm, 2333 Luguna St., San Francisco, Calif. 94115

[21] Appl. No.: 445,440

[22] Filed: Dec. 4, 1989

[51] Int. Cl.[5] .............................................. F25D 3/08
[52] U.S. Cl. ........................................... 62/530; 62/4; 128/402; 128/403
[58] Field of Search ...................... 128/402, 403; 62/4, 62/530

[56] References Cited

U.S. PATENT DOCUMENTS

| 3,091,091 | 5/1963 | Ferrante | 62/530 X |
|---|---|---|---|
| 3,095,291 | 6/1963 | Robbins | 62/530 X |
| 3,780,537 | 12/1973 | Spencer | 62/530 |
| 3,804,077 | 4/1974 | Williams | 62/64 X |
| 3,885,403 | 5/1975 | Spencer | 62/530 |
| 4,324,111 | 4/1982 | Edwards | 62/530 X |
| 4,404,820 | 9/1983 | Romaine | 62/530 |
| 4,462,224 | 6/1974 | Dunshee et al. | 62/530 |
| 4,596,250 | 6/1986 | Beisang, III et al. | 128/403 X |
| 4,854,319 | 8/1989 | Tobin | 128/402 X |
| 4,910,978 | 3/1990 | Gordon et al. | 62/530 |

Primary Examiner—Lloyd L. King
Attorney, Agent, or Firm—Thomas R. Lampe

[57] ABSTRACT

A two-compartment thermal pack for applying cold to an object including a particulate mixture of a solute and time-delayed gelling agent in one compartment and a liquid solvent in another compartment.

11 Claims, 2 Drawing Sheets

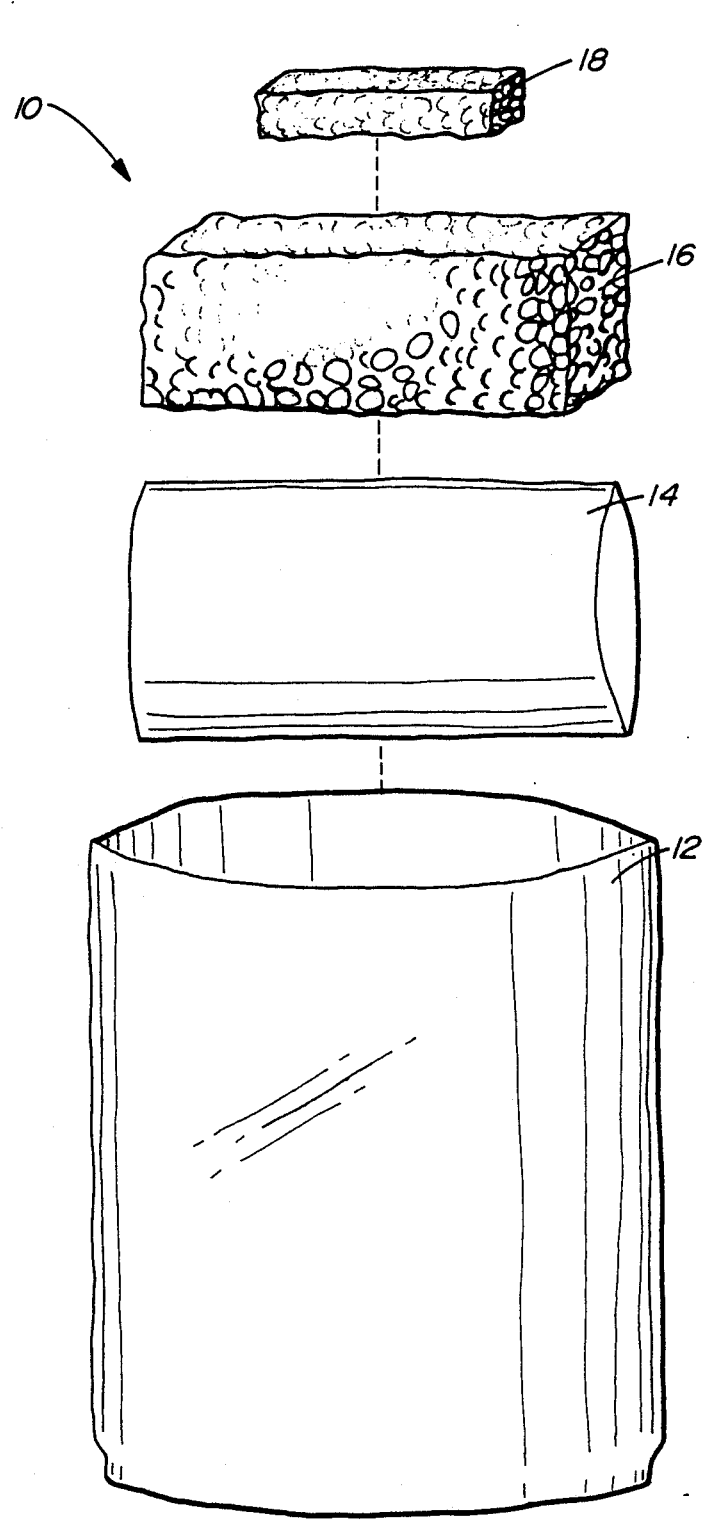
FIG._1

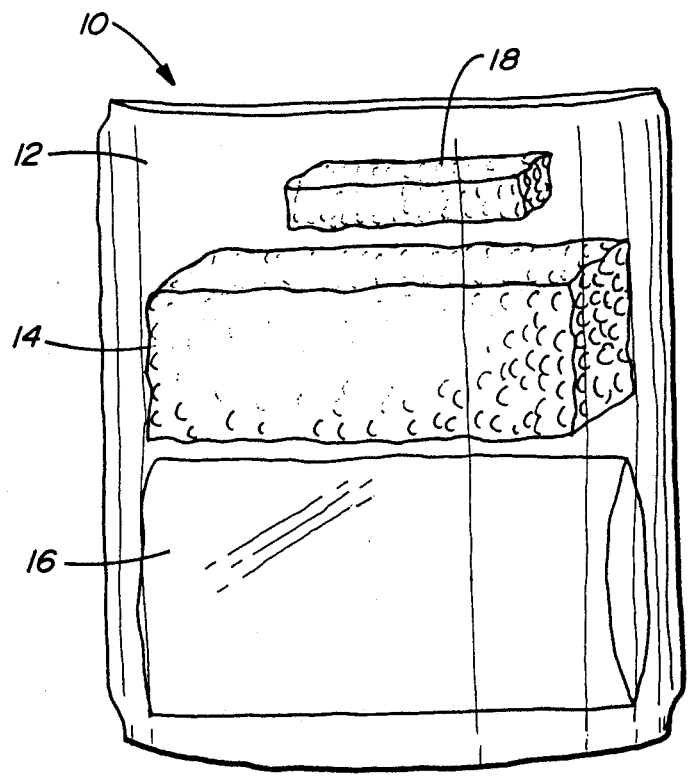
FIG._2

THERMAL PACK

TECHNICAL FIELD

This invention relates to a thermal pack for generating cold and applying cold to an object. The thermal pack is also capable of re-use as a cold pack.

BACKGROUND ART

Thermal packs are well known in the prior art. Generally speaking, there are two primary types of thermal or hot and cold packs.

There is the so-called instant pack wherein separated ingredients are combined and chemically react to liberate or absorb heat and thus produce heating or cooling.

There is also the type of thermal pack commonly referred to as the gel pack. Gel packs essentially comprise an outer flexible package containing a gel which is cooled by placing it in a freezer or the like. Gel packs have the advantage over most instant packs of being flexible or moldable even when frozen. However, conventional gel packs do not readily lend themselves to use with the types of chemicals employed in instant packs to liberate or absorb heat. Thus, for many years, the consumer was faced with the choice of purchasing and using either an instant pack or a gel pack, both of which had certain drawbacks and disadvantages.

U.S. Pat. No. 3,804,077 discloses an instant hot or cold pack which also forms a gel. Included in the pack is a first sealed compartment containing particles of a first material such as calcium chloride or ammonium nitrate (depending upon whether an exothermic or endothermic reaction is desired) and starch particles.

When the first material and starch are mixed with water dispensed from a ruptured second compartment of the pack, a gel is immediately formed. This immediate formation of the gel impedes movement of the materials in the pack. This is a drawback since restriction of movement of the materials slows the rate at which chemical reaction occurs and reduces both the rate and range of temperature change. Temperature of the pack can vary widely over the extent thereof. Use of starch, it is believed, also results in the pack becoming hard and inflexible when frozen.

U.S. Pat. No. 4,462,224 discloses a thermal pack which is said to overcome the disadvantages of the prior packs by combining the advantages of an instant hot or cold pack with the advantages of a reusable cold pack.

U.S. Pat. No. 4,462,224 discloses a three-compartment, instant, reusable cold pack for removing heat from an object. A first compartment contains a predetermined amount of solvent comprised primarily of water. A second compartment contains a predetermined amount of a particulate chemical solute capable of essentially completely dissolving in the solvent and reacting therewith whereby a predetermined amount of heat is absorbed. A third compartment contains a predetermined amount of gelling agent capable of gelling with the solvent and solute solution after the cold of the pack has disappeared and the pack reaches ambient temperature.

Mixing of the contents of the first compartment and the second compartment produces an instant cooling effect in the manner of a conventional instant cold pack. Once the solution has returned to ambient temperature, the contents of the third compartment are joined with the contents of the first and second compartments and manually kneaded and mixed to produce a gel that allegedly will remain flexible when cooled to temperatures typically attainable in a freezer.

The pack of U.S. Pat. No. 4,462,224 has a number of disadvantages. The package itself is relatively complex in that it incorporates three compartments. If the proper sequence of mixing is not followed the pack can be rendered useless. If the second and third compartment contents are mixed by mistake prior to mixing of the first and second compartment contents, the cooling and gelling functions either do not occur or occur on a limited basis or in an ineffectual manner.

The same holds true if all three compartment contents are mixed at the same time. The gel material impedes relative movement of the other chemicals in the pack, slowing down the rate of chemical reaction and thus reducing the ultimate temperature change available.

Such errors can readily occur, especially when one considers that thermal cold packs are often employed in emergency situations. Also with regard to the pack of U.S. Pat. No. 4,462,224, it should be pointed out that considerable effort must be expended by the user to produce the desired results. A great deal of manual manipulation must take place in order to bring the interiors of the compartments into communication in the proper manner as well as to mix same.

It should also be mentioned that the three compartment configuration employed in the device of U.S. Pat. No. 4,462,224 results in much of the overall surface area, e.g. one third, of the pack being rendered useless or non-operative when used as an instant hot or cold pack. That is, only the surface area corresponding to the first and second compartments may be usefully applied to an object during the instant pack phase. The remaining third compartment, which is not mixed until the cold has essentially disappeared, is cumbersome and likely to get in the way when the pack is being utilized in its instant mode.

Mixing of the contents of the third compartment with the previously mixed ingredients of the first and second compartments is also a time consuming and tedious process. The user must employ both hands to knead the material in the third compartment with the materials in the first and second compartments. Considerable time and energy must be expended to provide for a thorough mix.

DISCLOSURE OF THE INVENTION

In common with the arrangement disclosed in U.S. Pat. No. 4,462,224, the thermal pack of the present invention is also utilizable as either an instant cold pack or a reusable gel cold pack. In contrast to the prior art, however, the thermal pack of the present invention is characterized by its simplicity and ease of use. In particular, the thermal pack is of two compartment construction, insuring that proper mixing of the pack components will take place, even in rush or emergency situations.

Further, the two compartment construction of the present thermal pack permits effective usage thereof as an instant pack since virtually all of the outer pack surface can be placed in engagement with an object to apply cold thereto.

Importantly, although the present thermal pack incorporates a gelling agent, such agent does not interfere with the cooperative relationship between the chemical materials of the pack which are utilized to generate cold. That is, the gelling agent is of such a character that it will not interfere with either the mixing of the chemically reactive materials or impede the chemical reaction therebetween. Thus, the pack temperature decrease rate and range are maximized.

The aforesaid advantages are accomplished by incorporating in the thermal pack of the present invention a gelling agent of a specified character within the same compartment as the solute component of the chemically reactive materials utilized to produce cold. When a solvent is introduced into that compartment from the other compartment comprising part of the thermal pack, instant cold is produced.

The gelling agent will not interfere with the mixing of the reactive chemicals or their production of cold because the gelling agent will not actually form a gel until the cooling takes place and after the cold produced in the instant pack mode leaves the pack through normal use. When the gel is finally formed, the pack can be re-used by placing it in the freezing compartment of a refrigerator. Gel not only provides for effective cold retention but also readily conforms to the surface of an object, such as a human limb, to which the pack is applied.

A particular gelling agent found appropriate for use in connection with this invention is hydroxypropyl methylcellulose in particulate form which has not been "wetted out" or prewetted. Such material is not only non-chemically reactive with the thermal producing chemicals of the pack but has other advantages as well. Gel produced therefrom has a relatively high viscosity and thus will not "saddle bag" away from the area to be cooled.

Further, a gelling agent of this nature absorbs moisture within the solute with which it is mixed prior to addition of the solvent from the other or second compartment of the pack. Resident moisture in the solute chemical can interfere with the proper functioning thereof.

The gelling agent has a time delay capability, that is, it becomes a gel only after the cold produced by the reactive chemicals has dissipated, for example, in the order of 2-4 hours after initiating the thermal reaction, and thus will not interfere with either the mixing of, or chemical reaction between, the chemically reactive components.

U.S. Pat. No. 4,462,224 discloses the use of hydroxypropyl methylcellulose as a gelling agent employed in the third compartment of the thermal pack disclosed in that patent. However, the patent specifically teaches that the hydroxypropyl methylcellulose must be thoroughly pre-wetted by a wetting agent in order to operate properly.

Surprisingly, with respect to the present invention, it has been found that hydroxypropyl methylcellulose which has not been pre-wetted not only constitutes a suitable gelling agent but also, when employed in proper proportion by weight with respect to the solute and solvent components of the pack, provides the many important advantages indicated above.

Other features, advantages and objects of the present invention will become apparent with reference to the following detailed description and accompanying drawings.

BRIEF DESCRIPTION OF THE DRAWINGS

FIG. 1 is an exploded, elevational, diagrammatic view illustrating the components of a thermal pack constructed in accordance with the teachings of the present invention; and FIG. 2 is a view similar to FIG. 1 but illustrating the assembled thermal pack.

BEST MODE FOR CARRYING OUT THE INVENTION

Referring now to the drawing, FIG. 1 illustrates a thermal pack constructed in accordance with the teachings of the present invention prior to assembly thereof. The thermal pack includes a first container 12 in the form of a pouch formed of resilient plastic material such as polyethylene. A flexible outer wall of the first container is positionable against an object, such as a portion of a human body, to apply cold thereto. First container 12 defines a first interior.

The thermal pack also includes a second container 14 defining a second interior. Second container 14 is in the form of a closed bag constructed of rupturable material such as plastic sheeting. Second container 14 has disposed in the interior thereof a liquid solvent which may be water or other liquid primarily constituting water. Second container 14 is thin walled so that it is relatively easily rupturable upon application of outside force thereto. Upon assembly of the thermal pack of the present invention second container 14 is disposed within the interior of first container 12 as shown in FIG. 2.

Also disposed in the interior of first container 12 upon assembly of the thermal pack of the present invention is a mixture of particulate materials. The mixture includes a particulate solute 16 which will dissolve in the solvent contained in the second container 14 when the second container 14 is ruptured.

The solute is preferably ammonium nitrate. This results in a reaction with the solvent which is endothermic, i.e. cold is generated. Such chemical thermal reactive properties, are well known in the art.

Also included in the mixture of particulate materials in the first interior is a gelling agent 18 cooperable with the liquid solvent to produce a gel on a time-delayed basis whereby the gel will not interfere with the mixing of, or chemical reaction between, the solvent and solute 16 during generation of cold. In the completed pack the gelling agent and solute particles are commingled thoroughly.

A suitable gelling agent is particulate, non-prewetted hydroxypropyl methylcellulose.

Hydroxypropyl methylcellulose is a known gelling agent and in fact is noted as a gelling agent in U.S. Pat. No. 4,462,224. However, that patent teaches the use of such gelling agent only when prewetted and housed in a separate compartment from both the solute and the solvent. It is therefore surprising to find that hydroxypropyl methylcellulose may actually be premixed along with the particulate solute material at the time of thermal pack formation, remain stored with the particulate solute material, and still function as a gelling agent in such a way that it will not interfere with either the mixing of the solute and solvent or the chemical reaction therebetween.

In order for this desired effect to be obtained it has been found that the solute, solvent and gelling agent must have a specific proportionate relationship by weight. In particular, the particulate solute and liquid solvent are preferably employed in generally equal amounts by weight. The non-prewetted particulate hydroxypropyl methylcellulose preferably constitutes by weight generally from about 4% to about 25% of the solute in the mixture.

With the aforestated preferred proportionate relationship by weight it has been found that the non-prewetted hydroxypropyl methylcellulose becomes a gel within 2–4 hours, well after cold from the initial thermal chemical reaction has been exhausted.

After the particulate material mixture has been inserted into the interior of first container 12 along with second container 14, the first container is closed and sealed. To initiate the instant cold reaction, second container 14 is squeezed between the outer walls of first container 12 until the second container ruptures. The contents are then shaken or kneaded to work in the solvent.

It is preferred that yet two additional chemicals be incorporated in the particulate material mixture. It has been found that the incorporation of a metallic acetate such as aluminum sulfate and sodium chloride can not only further impede or delay the formation of a gel but result in a gel being formed which is quite firm and viscous, characteristics often desired.

A thermal pack having the following formulation has been found to have the desired characteristics just recited:

7.5 oz. Water
6 oz. Ammonium nitrate
From about 0.25 oz. to about 1.5 oz. Non-prewetted hydroxypropyl methylcellulose
From about 15 grains to about 40 grains Aluminum sulfate
0.5 oz. Sodium Chloride

What is claimed is:

1. A thermal pack for applying cold to an object, said thermal pack being operable to generate said cold and capable of reuse as a cold pack, said thermal pack comprising, in combination:

a first container including a flexible outer wall positionable against said object to apply cold thereto and defining a first interior;
   a second container defining a second interior adapted to be brought into communication with said first interior;
   a liquid solvent disposed in said second interior;
   a mixture of particulate materials in said first interior, said mixture including a solute soluble in said liquid solvent and chemically reactive therewith when said first and second interiors are in communication to substantially instantaneously generate cold, said mixture further including a gelling agent cooperable with said liquid solvent to produce a gel on a time-delayed basis whereby said gel will not interfere with the chemical reaction between said solvent and solute during generation of said cold.

2. The thermal pack according to claim 1 wherein said gelling agent is particulate cellulosic material.

3. The thermal pack according to claim 2 wherein said gelling agent is non-prewetted hydroxypropyl methylcellulose.

4. The thermal pack according to claim 1 wherein said gelling agent is non-chemically reactive with either said solvent or said solute.

5. The thermal pack according to claim 1 wherein said solvent is essentially water.

6. The thermal pack according to claim 1 wherein said solute is particulate ammonium nitrate.

7. The thermal pack according to claim 1 wherein said solute and said liquid solvent are in generally equal amounts by weight.

8. The thermal pack according to claim 7 wherein said gelling agent is particulate, non-prewetted hydroxypropyl methylcellulose and constitutes from about 4% to about 25% of said solute in said mixture.

9. The thermal pack according to claim 1 wherein said mixture further comprises a metallic acetate.

10. The thermal pack according to claim 9 wherein said metallic acetate is aluminum sulfate.

11. The thermal pack according to claim 1 wherein said mixture further comprises sodium chloride.

* * * * *